United States Patent [19]

Murakoshi et al.

[11] Patent Number: 4,517,976
[45] Date of Patent: May 21, 1985

[54] HIGH FREQUENCY SCALPEL AND ENDOSCOPE SYSTEM AND METHOD OF OPERATING SAME

[75] Inventors: Makoto Murakoshi, Asaka; Takahiro Ota, Tokyo, both of Japan

[73] Assignee: Fuji Photo Film Co., Ltd., Kanagawa, Japan

[21] Appl. No.: 424,769

[22] Filed: Sep. 27, 1982

[30] Foreign Application Priority Data

Oct. 20, 1981 [JP] Japan .................. 56-167567

[51] Int. Cl.³ .............................. A61B 17/39
[52] U.S. Cl. .................... 128/303.15; 128/4; 128/303.17
[58] Field of Search ........... 128/303.13, 303.14, 128/303.15, 303.17, 303.18, 4–8, 421, 804

[56] References Cited

U.S. PATENT DOCUMENTS

| | | | |
|---|---|---|---|
| 3,566,876 | 3/1971 | Stoft et al. | 128/421 |
| 3,942,530 | 3/1976 | Northeved | 128/303.15 |
| 4,204,528 | 5/1980 | Termanini | 128/6 |
| 4,228,809 | 10/1980 | Paglione | 128/804 |
| 4,453,547 | 6/1984 | Castel et al. | 128/421 |

FOREIGN PATENT DOCUMENTS 2621321 12/1977 Fed. Rep. of Germany ......... 128/4

Primary Examiner—Lee S. Cohen
Attorney, Agent, or Firm—Birch, Stewart, Kolasch & Birch

[57] ABSTRACT

A high frequency scalpel system for use with a video system such as an endoscope using an imaging device essentially consists of a therapeutic electrode functioning as a surgical knife, and a high frequency oscillator for supplying high frequency power to the electrode. In the coagulation operating mode of the scalpel, frequency modulated driving current is applied to an affected part of a living body intermittently only during a horizontal blanking period of a video signal transmitted in the video system. In the blend mode, a mixed mode of the cutting and coagulation modes, the frequency modulated driving current is fed to the scalpel electrode with its larger amplitude falling in a horizontal blanking period and its smaller amplitude in a horizontal scanning period of the video signal. The imaging device and its associated circuitry in the endoscope may be shielded electromagnetically.

15 Claims, 7 Drawing Figures

→ TIME

HIGH FREQUENCY SCALPEL AND ENDOSCOPE SYSTEM AND METHOD OF OPERATING SAME

BACKGROUND OF THE INVENTION

1. Field of the Invention

This invention relates to a high frequency scalpel system, and more particularly to a high frequency scalpel system including an electrode functioning as a scalpel proper and a high frequency oscillator circuit adapted for supplying high frequency current to the electrode, and also to an endoscope making use of such a high frequency scalpel system.

2. Description of the Prior Art

A high frequency scalpel may be used in a known manner for cutting an affected portion of a living body, or stopping bleeding thereat, by means of a Joule's heat generated at a portion thereof by supplying a high frequency current of a frequency ranging approximately from 300 kHz to 1 MHz between a scalpel or theraputetic electrode and a planar electrode contacted with the affected portion.

In general, a scalpel may work in three operating modes: cutting, coagulation and blend modes. In a cutting mode, an affected portion is cut out or incised under continuous application of high frequency current. In a coagulation mode, hemostasis is effected by protein coagulation of the affected portion resulting from intermittent application of high frequency current. A blend mode is a mixed mode of the cutting and coagulation modes. In any of these modes of the high frequency scalpel, a high frequency current with a maximum power output of several hundreds of watts and a peak voltage of approximately three thousand volts, by way of an example, is supplied to the electrodes. Hence, when a high frequency scalpel is used in conjunction with a medical TV system or an endoscope employing a solid state imager, a high frequency noises resulting from the operating current for the scalpel may be mixed into a video signal for the endoscope or TV system. This may cause flickers, smears or stripes in a picture displayed on a screen so as to make it difficult to view the picture on the screen.

For instance, in an endoscope employing a solid state imaging device such as a charge coupled device (CCD) or bucket brigade device (BBD), referred to as a charge transfer device (CTD), where a video signal line, adapted for transmitting a video signal from a solid state imaging device mounted in a viewing head of the endoscope is installed within an endoscope sheath in a side by side relationship with a high frequency power source line adapted for supplying a high frequency drive signal to the scalpel electrode mounted in the viewing head, electromagnetic coupling may be caused between the video signal line and the high frequency source line. In such a case, it may be difficult for an operator to view an endoscope image, that is, a picture, indicative of the inside of a cavity into which a viewing head of the endoscope is inserted, and displayed on a video display device such as cathode ray tube (CRT) provided in an operating unit of the endoscope.

SUMMARY OF THE INVENTION

It is an object of the present invention to provide a high frequency scalpel which avoids the aforementioned drawbacks of the prior art, and in which video signals transmitted in a video system will not be affected by noises in the coagulation and blend modes, and an endoscope making use of such a high frequency scalpel.

In accordance with the present invention, high frequency current is supplied to electrodes of a high frequency scalpel during horizontal blanking periods of a video signal transmitted in a video system.

A high frequency scalpel of the present invention has a control circuit by means of which high frequency current is supplied from a high frequency oscillator to electrodes of the high frequency scalpel during horizontal blanking periods of video signals transmitted from a raster scanning-type imaging system.

An endoscope making use of a high frequency scalpel according to the present invention includes a solid state imaging device operative for picking up an image inside a cavity of a living body to produce a corresponding video signal, a video display circuit operative to receive said video signal to visually display the image, a high frequency oscillator operative to supply a high frequency current to an electrode acting as a high frequency scalpel, and a control circuit operative to control the supply of high frequency current from the high frequency oscillator to the electrode in such a manner that the high frequency current is supplied during horizontal blanking periods of the video signal.

In the case of the NTSC standard television format, for example, each frame has 525 horizontal lines, and is made up of two interlaced fields with the frame period equal to 1/30 of a second. Hence, the period H of one horizontal scanning line is approximately 63 microseconds. The horizontal blanking period if approximately 11 microseconds, thus accounting for approximately 17 percent of the horizontal scanning period. The function of a high frequency scalpel will be sufficiently exhibited when the high frequency current pulses with the repetition period equal to 63 microseconds and pulse duration equal to 11 microseconds are supplied to an electrode unit of the scalpel in the coagulation and blend modes in timing with the horizontal blanking periods of the video signal.

BRIEF DESCRIPTION OF THE DRAWINGS

Those and other objects and features of the present invention will become more apparent from a consideration of the following detailed description in conjunction with the accompanying drawings in which.

DESCRIPTION OF THE PREFERRED EMBODIMENT

Figure 1:
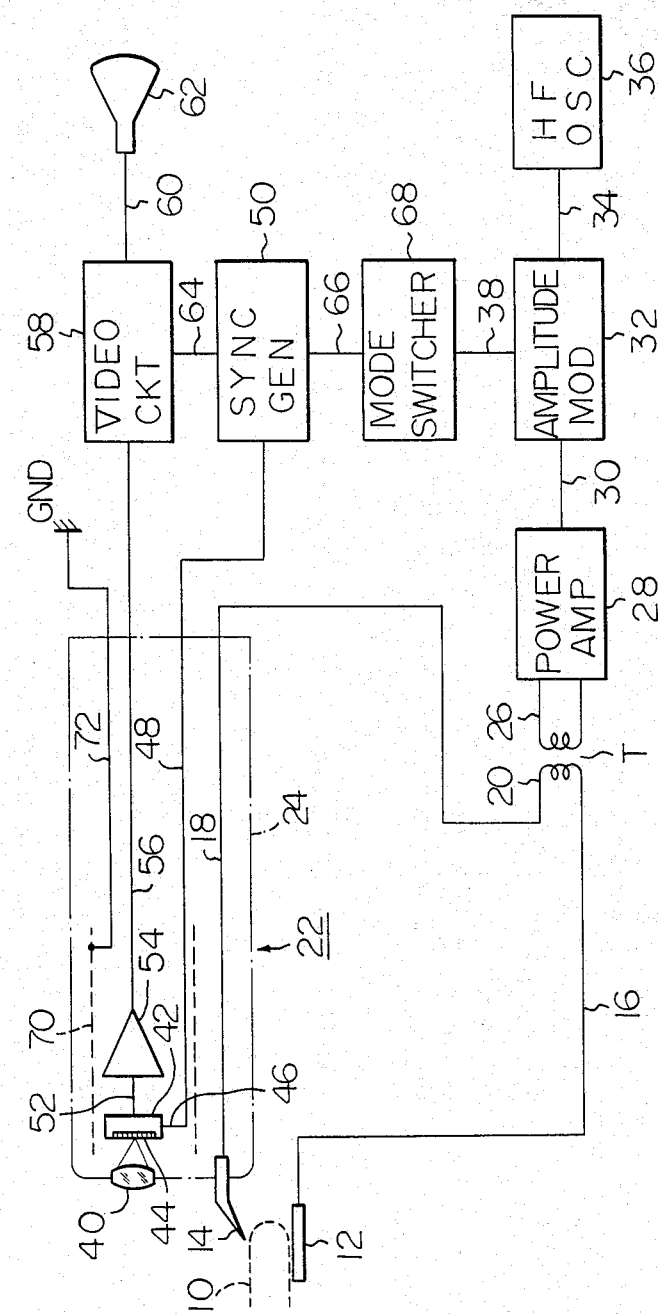
FIG. 1 is a schematic block diagram showing an embodiment of the present invention in which a high frequency scalpel is applied to an endoscope making use of a solid state imaging device.

FIG. 1 shows an example in which a high-frequency scalpel in accordance with the present invention is applied to an endoscope using a solid state imaging device. In the figure, a planr electrode 12 and a therapeutic electrode 14, both of which are to be contacted with an afflicted portion 10 shown by a dotted line in the figure, are respectively connected by leads 16 and 18 across output or secondary winding 20 of a booster transformer T for cutting d.c. components of current supplied to electrodes 12 and 14. The therapeutic electrode 14, functioning as a surgical knife or scalpel proper, is provided at the end of a sheath 24 of an endoscope 22. Sheath 24 is shown schematically by a chain-dotted line in the figure. Lead 18 is passed from electrode 14 through the inside of the sheath 24 to be connected at the other end of sheath 24 to the booster transformer T.

An input or primary winding 26 of the transformer T is connected to the output of a power amplifier circuit 28, the input of which is connected to the output of an amplitude modulation circuit 32. The circuit 32 has its one input connected to a high frequency oscillator 36.

Figure 2A:
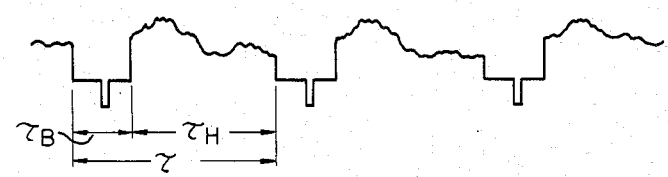
FIG. 2 is a diagram showing signal waveforms appearing at the points of the circuits shown in FIG. 1.

The oscillator 36 is adapted to produce high frequency signals at a frequency e.g. of 300 kHz to 1 MHz. FIG. 2D shows a signal waveform appearing on the output lead 34. This high-frequency signal is received by the one input 34 of the modulation circuit 32 as a carrier wave, which is amplitude modulated by modulating signals, shown in FIG. 2B or 2C, supplied to the other input 38, as later described. The amplitude modulated signal, which has the waveform as shown in FIG. 2E or 2F, is supplied to the lead 30 as an output signal thereof. By the power amplifier 28, the output signal from the lead 30 is power amplified for supplying a driving current to the therapeutic electrode 14 and the planar electrode 12. Through the boosting transformer T, d.c components are removed from the driving current, with the voltage appearing across secondary winding 20 of the transformer T ultimately reaching one hundred to several thousands volts.

In the present embodiment, an objective lens 40 and a solid state imaging device 42 are provided to the foremost part of the endoscope 22. The imaging device 42 is has an array of pixels 44 located in the focal plane of the objective lens 40, and designed to pick up an image inside a cavity or opening of a living body focussed by the lens 40. The imaging device 42 may be a charge transfer device (CTD) such as a charge coupled device (CCD) or bucket brigade device (BBD). In FIG. 1, solid state imaging device 42 is shown schematically as having a two-dimensional array or matrix 44 of a number of photosensitive cells, called picture elements, or pixels.

The imaging device 42 has its driving input port 46 connected to one output of a synchronous generator 50 by a lead 48, which passes through the sheath 24. The imaging device 42 also has its video signal output port 52 connected via amplifier 54 and lead 56 to one input of a video circuit 58 located usually outside of the sheath 24. This lead 56 is also passed through the inside of the sheath 24 substantially in parallel to the leads 18 and 48. The video circuit 58 has its output 60 connected to an picture display device 62 such as cathode ray tube (CRT).

Synchronous clock pulses are supplied from the sync generator 50 over the lead 48 for driving, or clocking, the solid state imaging device 42, and also to the video circuit 58 from another output 64 of the sync generator 50. The imaging device 42 is responsive to the synchronous clock pulses received at the input port 46 for producing video signals at the video signal output port 52. These video signals, which are raster scanned, time serial signals representative of an image formed on array of pixels 44, are supplied to the video circuit 58 via amplifier 54 over lead 56 to be displayed as a visual image on an picture display device 62.

The video signals supplied to the video circuit 58 on lead 56 may include luminance signals for three elementary colors, that is, red (R), green (G) and blue (B). The signal channel composed of the amplifier 54 and the lead 56 shown in FIG. 1 might then be thought to represent three discrete signal channels for the respective elementary color luminance signals. Alternatively, the amplifier 54 may include a matrix circuit for combining the three color signals into composite video signals in accordance with the NTSC standard television format. In the latter case, the composite video signals of the NTSC format are transmitted over the lead 56, and the video circuit 58 includes a matrix circuit for separating the composite video signals into luminance signals for the three elementary colors. In any case, the video signal transmitted over the lead 56 has a pulse repetition period $\tau$ for each horizontal scanning line H of a frame, as shown schematically by a somewhat simplified waveform in FIG. 2A. This period $\tau$ is equal in a known manner to 63 microseconds where a single frame has 525 horizontal scanning lines, and is composed of two interlaced fields with the frame period equal to 1/30 of a second. Usually, the horizontal blanking period $\tau_B$ accounts for approximately 17 percent of the horizontal scanning period $\tau$, and is equal to about 11 microseconds.

According to the present invention, the high frequency current for driving the therapeutic electrode 14 is supplied to it over lead 18 only during the horizontal blanking period of the video signal to remove the effects of the high frequency current over the lead 18 onto the video signal on the lead 56 in the manner described below.

Since the lead 18 designed to supply high frequency current to the therapeutic electrode 14 is passed through the inside of the sleeve 24 of the endoscope 22 substantially in parallel to the lead 56 for transmitting the video signal, there exits an electromagnetically inductive coupling between these leads 18 and 56. Thus the video signal transmitted on the lead 56 is likely to be affected by the high frequency signal transmitted through the lead 18. Leakage of high frequency signals also occurs from the high frequency circuitry including the high frequency oscillator 36, the therapeutic electrode 14, the planar electrode 12 and power amplifier 28. Thus the video system composed of the imaging device 42, amplifier 54, lead 56 and the video circuit 58 is subject to noises from the high frequency circuit. These noises give rise to dots, smears and stripes on a picture on the display screen of the video display device 62 thus making it difficult to view the picture.

According to the present invention, however, a third output 66 of the sync generator 50 is connected through a mode switching circuit 68 to a modulating signal input 38 of the amplitude modulation circuit 32. At the output 66 of the sync generator 50, there is produced a signal synchronized with the horizontal scanning period $\tau_B$ of the video signal. The mode switching circuit 68 is responsive to two modes, coagulation mode and blend mode, of the high frequency scalpel. Mode switcher 68 is timed with the horizontal blanking period $\tau_B$ to selectively supply one of two kinds of signal waves to the input terminal 38 of the amplitude modulation circuit 32 during the blanking period $\tau_B$.

Figure 2B:

For example, when the high frequency scalpel system is set to the coagulation mode, a modulating signal shown in FIG. 2B is produced by the switching circuit 68 on the lead 38. This signal wave is a rectangular pulse wave that may take binary voltages 0 and V1 with its high level period substantially coinciding with the horizontal blanking period $\tau_B$ of the video signal (see FIG. 2B). The amplitude modulation circuit 32 modulates the amplitude of a high-frequency signal, i.e. a carrier (FIG. 2D), generated from the high frequency oscillator 36, with the modulating signal (FIG. 2B) with a modulation factor of 100 percent to provide a modulated wave shown in FIG. 2E to the power amplifier 28. Accordingly, the therapeutic electrode 14 and the planar electrode 12 are driven by the high frequency current in timing with the horizontal blanking period $\tau_B$ of the video signal supplied from the solid state imaging device 42. Thus, an analog waveform during a horizontal scanning period $\tau_H$, FIG. 2A, of the video signal is not affected by any noise produced by the high frequency current.

Figure 2C:
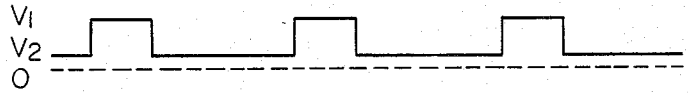
Figure 2D:
Figure 2E:
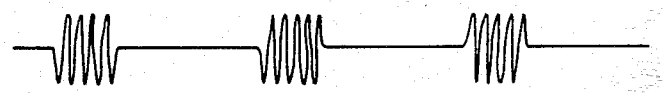
Figure 2F:
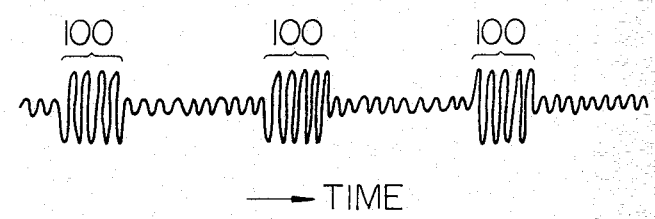

When the high frequency scalpel is set to the blend mode, a modulating wave shown in FIG. 2C is produced on the lead 38 by the mode switching circuit 68. This modulating wave is a rectangular pulse wave that may take binary voltages V1 and V2 that are not zero, with its HIGHER LEVEL V1 occurring during the horizontal blanking period $\tau_B$ of the video signal (FIG. 2A). The amplitude modulation circuit 32 operates to amplitude modulate the high frequency signal from the oscillator 36 (FIG. 2D) with the modulating signal (FIG. 2C) to provide an output waveform which is a high frequency driving signal with a modulation index less than 100 percent, as shown in FIG. 2F. The power amplifier 28 power amplifies that waveform to drive the electrodes 14 and 12 in the blend mode. The drive current has its higher power portion 100 (FIG. 2F) synchronized with the horizontal blanking period $\tau_B$ of the video signal supplied from the solid imaging device 42. In other words, the timing of the high power portion 100 coincides with the horizontal blanking period $\tau_B$. The video signal is, therefore, not affected by any strong noise caused by the drive signal.

In accordance with the present embodiment, the solid state imaging device 42 in the foremost part, or viewing head, of the endoscope 22 and the associated circuits such as amplifier 54 are surrounded by a metallic tube shown only schematically by a dotted line 70. This tube is connected to a reference potential, e.g. ground GND, by a lead 72 for electromagnetically shielding and protecting the imaging device 42 and the related circuits from adverse effects of the high frequency circuitry. In this manner, any mixing of high frequency noises into the video signal supplied from the imaging device will be prevented more effectively.

While the foregoing description has been made with reference to an application of the inventive high frequency scalpel to an endoscope employing a solid state imaging device, the present invention is not limited to such an application. For example, the present invention may be applied to the case of using the high frequency scalpel with a medical or industrial televison camera system employing an image pick-up tube or a solid state imaging device. The present invention may also be applied to the case of using a high frequency scalpel not only in connection with a solid state imager but in connection with any other imaging system of the raster scanning type such as an image pickup tube.

The high frequency scalpel of the present invention makes it possible to minimize the effects of a high frequency scalpel driving signal on a video signal, and hence the effects of noises on an image displayed on a display screen. Hence, by using the high frequency scalpel of the present invention in conjunction with an endoscope making use of a solid state imaging device, a much clearer and higher quality endoscope image can be obtained on a video display device.

While there has been shown and described above an illustrative embodiment of a high frequency scalpel and an endoscope employing it in accordance with the invention, it will be appreciated that the invention is not limited thereto. Accordingly any modifications, variations or equivalent arrangements within the scope of the attached claims should be considered to be within the scope of the invention.

What is claimed is:

1. A high frequency scalpel system usable with a video imaging system developing a video signal comprising:
   an electrode functioning as a surgical knife;
   high frequency current supplying means for supplying said electrode with a high frequency current; and
   synchronous generator means for producing a synchronous signal which defines horizontal blanking periods in a raster scanning-type video signal;
   control means for enabling said high frequency current supplying means in response to the synchronous signal developed by said synchronous generator means so as to supply said electrode with the high frequency current primarily during a horizontal blanking period of the video signal.

2. A scalpel system in accordance with claim 1, wherein said high frequency current supplying means comprises amplitude modulator means for amplitude modulating the high frequency current with the synchronous signal.

3. A scalpel system in accordance with claim 2, wherein said high frequency current supplying means comprises mode selection means for selecting either one of coagulation and blend modes of operation for the scalpel system, said mode selection means being responsive to the development of said blanking periods of said synchronous signal to control said amplitude modulator means so that said modulator means amplitude modulates said high frequency current, when the coagulation mode is selected by said selection means, with a modulation factor substantially equal to a hundred percent, and, when the blend mode is selected by said selection means, to control said amplitude modulator means to modulate said high frequency current during said blanking periods of said synchronous signal with a modulation factor of substantially a hundred percent and during the remainder of said synchronous signal to modulate said high frequency current with a modulation factor substantially less than a hundred percent.

4. An endoscope comprising:
   an elongated, flexible tube having a viewing head portion to be inserted into a cavity;
   an electrode supported with the viewing head portion of said tube and functioning as a high frequency scalpel;
   a solid state imaging device provided in the viewing head portion of said tube for picking up an image of the inside of the cavity to produce a raster scanning video signal representative of the image;
   visualizing means for receiving the video signal to visualize the image on a display;
   high frequency current supplying means for supplying a high frequency current to said electrode;
   synchronous generator means for producing a synchronous signal to supply said imaging device with the synchronous signal so that said imaging device develops the video signal in synchronism with the synchronous signal; and control means for enabling said high frequency current supplying means in response to said synchronous signal developed by said generator means so as to supply said electrode with the high frequency current primarily during a horizontal blanking period of the video signal.

5. An endoscope in accordance with claim 4, wherein said synchronous generator means produces a clock signal to drive said solid state imaging device and a modulating signal which is in synchronism with a horizontal blanking period of the video signal, said high frequency current supplying means comprising amplitude modulator means responsive to the modulating signal for amplitude modulating the high frequency current with the modulating signal.

6. An endoscope in accordance with claim 5, wherein said high frequency current supplying means comprises mode selection means for selecting either one of coagulation and blend modes of operation for the scalpel, said selection means being responsive to the modulating signal to control said modulator means so that said modulator means amplitude modulates the high frequency current, when the coagulation mode is selected by said selection means, with a modulation factor substantially equal to a hundred percent, and, when the blend mode is selected by said selection means, to control said amplitude modulator means to modulate said high frequency current during said blanking periods of said synchronous signal with a modulation factor of substantially a hundred percent and during the remainder of said synchronous signal to modulate said high frequency current with a modulation factor substantially less than a hundred percent.

7. An endoscope in accordance with claim 4, further comprising shielding means for electromagnetically shielding at least said imaging device from the high frequency scalpel.

8. An endoscope comprising:
an elongated, flexible tube having a viewing head portion to be inserted into a cavity of a living body;
a solid state imaging device provided in the viewing head portion for picking up an image of the inside of the cavity to produce a video signal representative of the image picked up;
synchronous generator means for generating a clock signal to drive said imaging device in a raster scanning fashion;
visualizing means for receiving the video signal to visualize the image on a display;
an electrode supported with said viewing head portion and working as a surgical knife;
high frequency current supplying means for supplying said electrode with a high frequency current; and
control means operative in response to the clock signal generated by said synchronous generator means for controlling said current supplying means so as to supply said electrode with the high frequency current primarily during a horizontal blanking period of the video signal.

9. An endoscope in accordance with claim 8, wherein said synchronous generator means generates a modulating signal in synchronism with a horizontal blanking period of the video signal, said control means comprising amplitude modulator means for amplitude modulating the high frequency current with the modulating signal.

10. An endoscope in accordance with claim 9, wherein said control means comprises mode selection means for selecting either one of coagulation and blend modes of operation for the surgical knife, said selection means being responsive to the modulating signal to control said modulator means so that said modulator means amplitude modulates the high frequency current, when the coagulationmode is selected by said selection means, with a modulation factor substantially equal to a hundred percent, and, when the blend mode is selected by said selection means, to control said amplitude modulator means to modulate said high frequency current during said blanking periods of said synchronous signal with a modulation factor of substantially a hundred percent and during the remainder of said synchronous signal to modulate said high frequency current with a modulation factor substantially less than a hundred percent.

11. An endoscope in accordance with claim 8, further comprising metallic enclosure means connected to a reference potential for enclosing at least the sides of said imaging device to electromagnetically shield said device from the high frequency current.

12. A scalpel and sensing system comprising:
an electrode functioning as a surgical knife;
high frequency drive means for supplying high frequency current to said electrode;
means for sensing an image adjacent said electrode, said means for sensing being adversely affected by said high frequency current;
pulse generator means for producing a pulse train, each pulse of said train defining a blanking period for said means for sensing;
inhibit means for disabling said means for sensing during each pulse developed by said pulse generator means; and
control means for enabling said high frequency drive means only during the development of each pulse by said pulse generator means.

13. A scalpel and video system comprising:
an electrode functioning as a surgical knife;
high frequency drive means for supplying high frequency current to said electrode;
a video information system, said video information system developing a raster scan video signal having display scans adversely affected by said high frequency current;
synchronous generator means for producing horizontal blanking periods in said raster scan video signal; and
control means for enabling said high frequency current supplying means in response to said synchronous generator means for supplying said high frequency current to said electrode primarily during the horizontal blanking periods in said raster scan video signal.

14. A method of substantially simultaneously operating a high frequency scalpel and a sensing system comprising:
driving the sensing system to develop a video signal;
producing a pulse train, each pulse of said train defining a blanking period of said video signal;
inhibiting said sensing system primarily during said blanking period; and
applying high frequency current to said scalpel primarily during said blanking period to operate said scalpel to thereby minimize adverse effects on said sensing system.

15. The method of claim 14 wherein said sensing system includes a raster scanned video display; said pulse train being a synchronization signal defining the horizontal blanking periods of said raster scanned video display.

* * * * *